United States Patent [19]

Stivender et al.

[11] 4,358,856
[45] Nov. 9, 1982

[54] MULTIAXIAL X-RAY APPARATUS

[75] Inventors: Paul M. Stivender; David M. Barrett, both of Brookfield, Wis.

[73] Assignee: General Electric Company

[21] Appl. No.: 202,094

[22] Filed: Oct. 31, 1980

[51] Int. Cl.³ .............................................. G03B 41/16
[52] U.S. Cl. ..................................... 378/167; 378/189; 378/197
[58] Field of Search ............... 250/468, 523, 525, 490, 250/491, 445 R, 446, 447, 448, 449

[56] References Cited

U.S. PATENT DOCUMENTS

| | | | |
|---|---|---|---|
| 3,281,598 | 10/1966 | Hollstein | 250/523 |
| 3,803,417 | 4/1974 | Kok | 250/490 |
| 3,803,418 | 4/1974 | Holstrom | 250/491 |
| 3,892,967 | 7/1975 | Grady | 250/447 |
| 4,288,700 | 9/1981 | Grass | 250/523 |

Primary Examiner—Craig E. Church
Attorney, Agent, or Firm—Ralph G. Hohenfeldt

[57] ABSTRACT

X-ray apparatus for angiography has a support member which is rotatable about a vertical axis and a U-shaped arm mounted on the support for rotating about a horizontal axis. A radially movable carriage with an x-ray source mounted on it is mounted at one end of the U-arm. Carriages which are movable linearly and radially relative to the horizontal axis support an image intensifier and a film changer respectively. The horizontal axis and vertical axis of rotation which is coincident with the x-ray beam axis intersect at a point which is isocentric. Images can be obtained with either the intensifier receptor or film changer receptor in varying degrees of magnification and without magnification while the patient being examined remains coincident with the isocenter. Means are provided for counterbalancing the source, changer and the intensifier independently. Force limited actuators such as motors equipped with slip-clutches are operatively coupled to counterweight cables for driving the carriages and for allowing the carriage to be moved manually. Any carriage has a tendency to remain where it is positioned because of independent counterbalancing and the entire U-arm remains balanced in all of its angular positions and for any position of the receptors or source.

15 Claims, 7 Drawing Figures

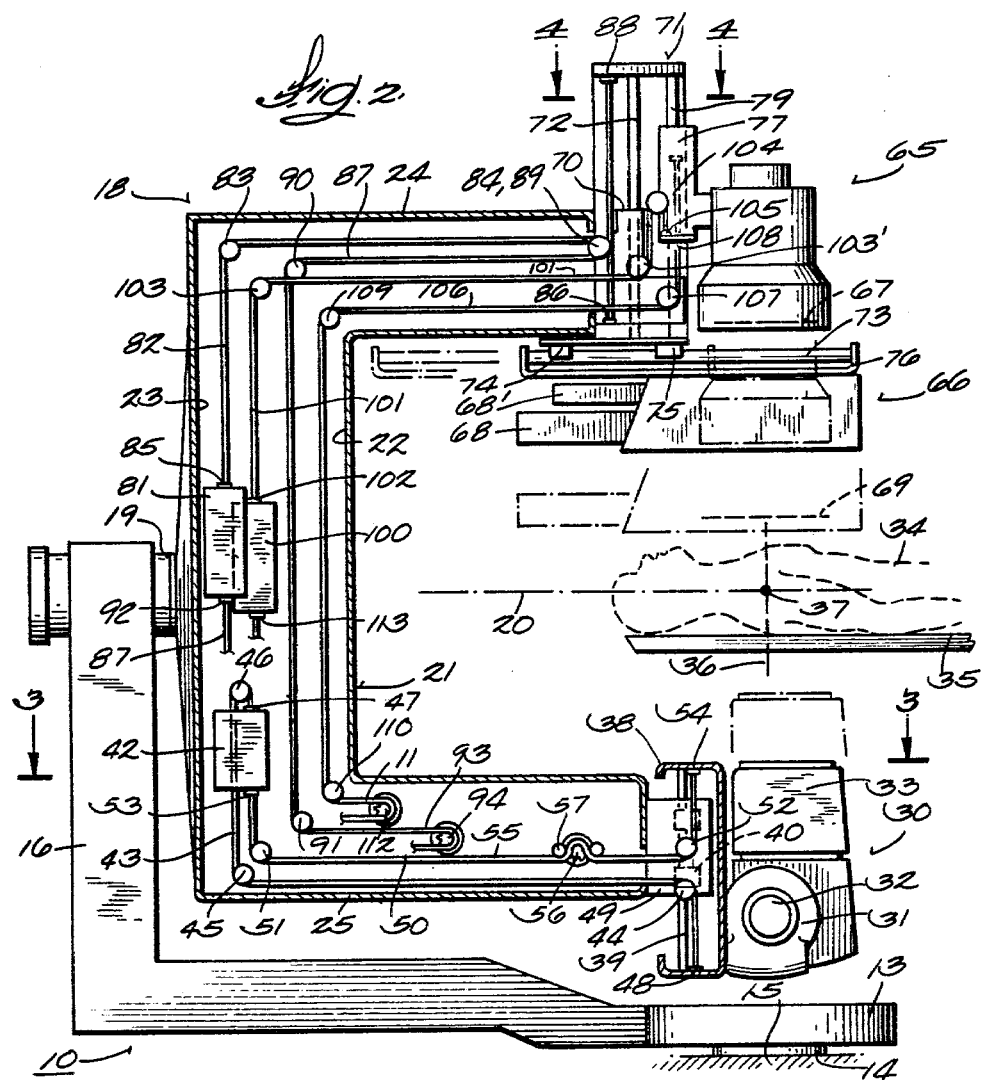
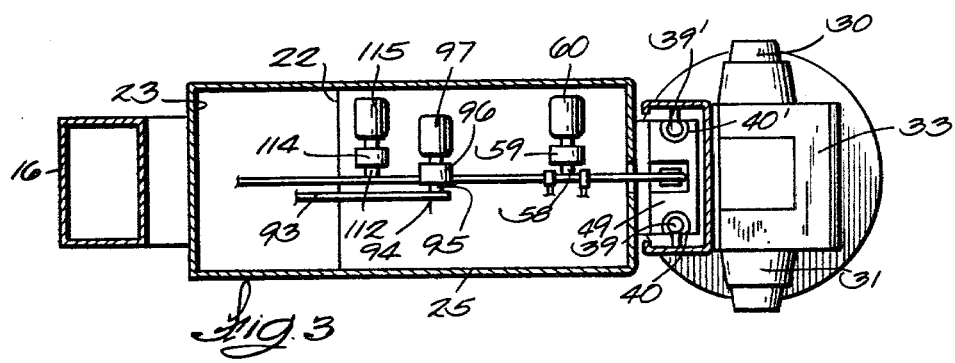

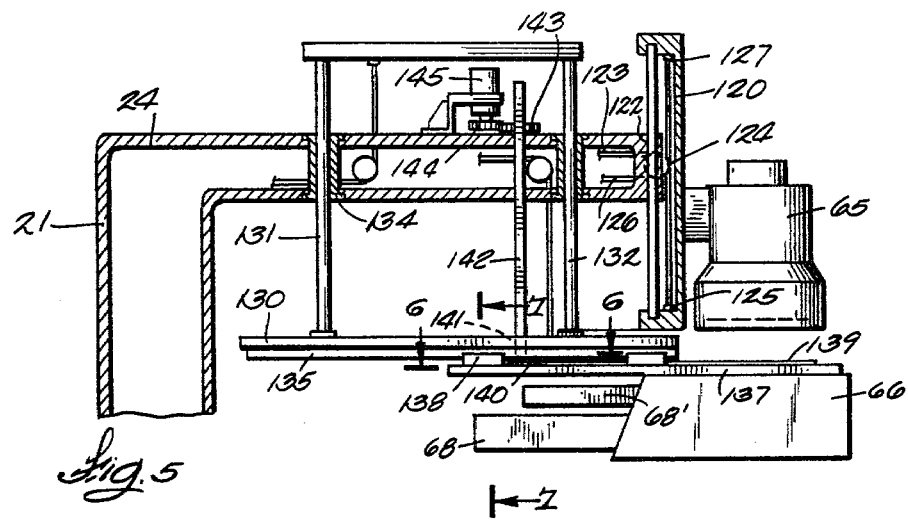
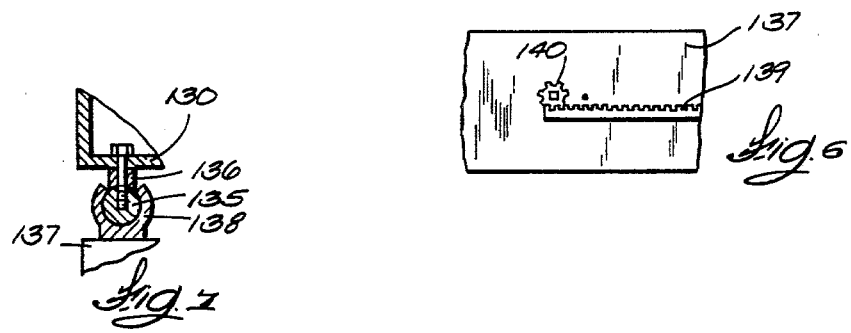
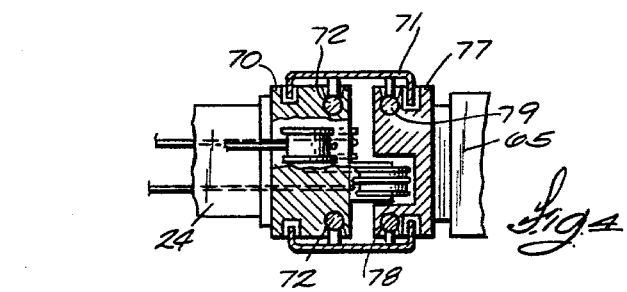

MULTIAXIAL X-RAY APPARATUS

BACKGROUND OF THE INVENTION

The apparatus disclosed herein is for performing x-ray examinations of the blood vessels and associated anatomy of the human body or, stated in another way, for performing angiographic procedures.

In general, apparatus that is designed especially for angiographic procedures, including both fluoroscopic viewing of the anatomy and recording of the images seen in various phases of the examination, must provide for angulating the axis of the x-ray beam from the frontal projection through a plurality of oblique projections to the lateral projection and through a plurality of head-to-foot angulations to at least 45°-50° in concert with the frontal and oblique angulations. The foregoing characterizes the class of diagnostic x-ray apparatus known as "multiaxis" angiographic apparatus.

During angiographic procedures, catheters, electrocardiograph leads and other devices are often connected to the patient. This makes is inconvenient for the x-ray technician working with the examining physician to move the patient and increases risk to the patient if gross movements are necessary. The desirability of being able to form most complete angiographic examinations which includes the views wherein the receptor is in close proximity (called contact) and those views wherein the receptor is at some greater distance from the patient (called magnification) without repositioning the patient or patient supporting table or hoisting the entire angulation apparatus on which the patient is supinely supported has been generally recognized, but until the apparatus disclosed herein was designed, this desirable objective has only been achieved at the expense of compromised x-ray source-to-image distance (SID) for magnification or contact angiography or both. If, as is the case with prior art angiographic apparatus, the patient must be raised or lowered significantly above or below normal x-ray table height to accommodate restrictions in the apparatus on positioning the x-ray source or receptors for the most advantageous x-ray view, the patient may then be in a position where it becomes inconvenient or awkward for the physician to work on the patient.

The apparatus disclosed herein is provided with one x-ray source and two image receptors, one of which is an x-ray image intensifier for examining the blood vessels fluoroscopically and the other of which is a radiographic film recording device such as a rapid film changer. The term "x-ray image intensifier" as used herein is intended to include any device that enables optical viewing of an x-ray image or, in other words, enables fluoroscopy to be performed. Maximum diagnostic information becomes available to the examining physician if the apparatus permits contact radiography and fluoroscopy and magnification radiography and fluoroscopy. In the magnification mode, the patient is customarily established about midway between the x-ray tube focal spot, which is the source, and the input plane of either the radiographic film or image intensifier. The focal spot-to-image receptor distance or SID for standard procedures is about 100 cm. This provides an image magnification factor of about 1.8 to 2.0. For contact radiography, where magnification is minimized, the intensifier or film changer input plane is moved closer to the body in which case it is desirable to maintain the same SID as is used in the magnification mode.

The preference is, of course, to be able to make fluoroscopic examinations with the image intensifier and, alternatively, make film recordings by means of a film changer with minimum or maximum permissible magnification with rotational angulations from posterior-anterior (PA) through oblique views to lateral being accomplished rotationally about a point in space called the isocenter which is centered at the anatomical area of interest. There is existing multiaxial x-ray apparatus that has an image intensifier and a rapid film changer mounted on a gantry along with an x-ray tube for enabling obtaining fluoroscopic and radiographic images at various angular aspects. However, prior art apparatuses have various disadvantages such as, when a constant SID for various magnifications is desired, there must be movement of the isocenter away from the anatomical center of interest. Or, the movement of both the intensifier and the film changer radially with respect to the isocenter is not independent and, therefore a major realignment of the common receptor carriage is required in addition to interchanging the receptors.

In one prior art angiographic apparatus design, for example, two image receptors, namely a rapid film changer and an image intensifier are mounted in a cluster at one place on a gantry in spaced relationship to an x-ray source which is mounted at another place. Switching the image intensifier input plane and the film changer input plane into perpendicularity with the x-ray beam axis is accomplished by mounting the changer and intensifier on the same pivotal support. At one rotational position of the support, the x-ray beam axis will be perpendicular to the intensifier's image plane and will be parallel to the image plane of the film changer since the intensifier and film changer planes are at a right angle with respect to each other. At the other rotational position of the common support the image plane of the film changer is in perpendicularity with the x-ray beam axis while at the same time the image plane of the intensifier is in parallel with the beam axis and on the side of the beam. One disadvantage of the rotatable cluster design is that the image intensifier or film changer, when rotated, can strike the patient. Curved guards have been used to reduce the likelihood of doing injury to the patient and contact sensors should be used to lock the cluster against rotation if patient contact is made. In any event, it is preferable to lower the patient away from the cluster before rotating the receptors, to make sure the patient is cleared, and then restore the patient to the position in which the radiographic views are to be made. This extends a time for making a complete examination undesirably.

Another prior art angiographic apparatus design has an image intensifier mounted on a gantry for movement of its image plane perpendicular to the x-ray beam axis. A film changer is mounted on the gantry adjacent the intensifier for being moved linearly and into perpendicularity with the x-ray beam axis provided that the intensifier has been retracted axially. The apparatus which incorporates this feature, however, has its components, namely, the receptors and x-ray source physically related in such a manner that it is not possible to maintain the x-ray beam axis in perpendicularity with the image receptor planes for many of the angles in which the x-ray beam axis may be directed.

A significant disadvantage in prior art angiographic apparatus results from the manner in which the x-ray source and the image intensifier and film changer are mounted on the gantry for enabling interchange of the intensifier and changer. Prior art mounting schemes result in the gantry, or other structure which supports the image intensifier, changer and x-ray source, going out of balance when any of these components is moved to enable one or another of the operating modes. The fact that movement of a component causes severe unbalance requires that the gantry and the component on the gantry be driven by powerful motor drive systems that can overcome any amount of unbalance of the heavy load. Use of high power drive systems can result in injury if one of the components is driven into the patient. Hence, these systems require highly reliable sensing devices which cause the motors to stop before a patient becomes seriously compressed.

SUMMARY OF THE INVENTION

In accordance with an illustrative embodiment of the invention, multiaxial x-ray apparatus has two image receptors, an image intensifier and a rapid film changer mounted on a gantry in spaced relationship with an x-ray tube that is also mounted on the gantry. The intensifier, film changer and x-ray tube are mounted for moving independently of each other. The gantry used to illustrate the invention has some known feaures in that it comprises a U-shaped arm having the intensifier and film changer image receptors mounted adjacent each other at one free end of the arm and an x-ray source mounted on the other free end. The unitary U-arm is mounted for rotation about a horizontal axis on an overhead or, optionally, floor-mounted member that rotates about a vertical axis. As illustrated, the U-arm is mounted to an L-shaped arm whose horizontal section or leg is journaled for rotation about a vertical axis in parallel with the floor.

The movable x-ray image intensifier, film changer and x-ray source are all counterbalanced so that the U-arm remains in balance when any of the intensifier, film changer or x-ray source is moved radially inwardly or outwardly with respect to the horizontal rotational axis of the U-arm. Counterbalancing enables the image intensifier or the film changer receptors or the x-ray source to be moved manually with little effort. However, motor assisted drive or actuation of each of the three components is also provided. The motors are low-powered since they only have to overcome any minor frictional force which may be inherent in the source and receptor mountings. The low-power actuation systems reduce the likelihood of a patient being injured if a component is driven into a patient. Force limited actuator means are used to move the components. By way of example, the receptors and source are driven through slip clutches in the illustrated embodiment, which are set to slip and limit driving force if they encounter any resistance in excess of minor frictional and inertial resistance. The clutch settings are such that they will slip if the component which they drive is moved manually. Thus, the driving and resisting force of the actuating means can be overcome by a small manual force on a receptor or the source. A benefit of this arrangement is that if a motor fails examination of a patient may still be completed since the receptors and source are movable manually. Moreover, if a part of the force limited actuator means such as a motor or clutch fails, none of the components will move into contact with the patient since they are fully counterbalanced. Force limiting actuator means, other than slip clutches, will be discussed later.

A significant feature of the new multiaxial angiographic apparatus is that substantially all examination procedures comtemplated by the physician can be carried out with the patient remaining at a constant level in coincidence with an isocenter. The isocenter is the point at which the horizontal rotational axis of the U-arm, the vertical rotational axis of the support or L-arm and the x-ray beam axis intersect. A further significant feature of the apparatus is that it permits obtaining x-ray views with an image intensifier and a film changer with various amounts of magnification at a constant SID. Contact imaging, that is, low magnification imaging where the receptor is near or substantially in contact with the patient, is also easily obtainable since the x-ray source and receptors are each independently movable relative to the isocenter. High magnification with constant SID such as 100 cm. is easily obtainable since provision is made for driving the x-ray source and the receptors in unison and in opposite direction relative to the isocenter.

How the foregoing and other more specific features of the invention are achieved will be evident in the more detailed description of a preferred embodiment of the multiaxial angiographic apparatus which will now be set forth in reference to the drawings.

DESCRIPTION OF THE DRAWINGS

FIG. 2 is a side elevation view of the apparatus with parts in section;

FIG. 3 is a sectional view taken on a line corresponding with 3—3 in FIG. 2;

FIG. 4 is a partial sectional view taken on a line corresponding with 4—4 in FIG. 2;

FIG. 5 shows an alternative structure for mounting an x-ray image intensifier and a film changer on a U-arm which is shown partially and in section;

FIG. 6 is a partial section taken on a line corresponding with 6—6 in FIG. 5; and FIG. 7 is a section taken on a line corresponding with 7—7 in FIG. 5 for illustrating one of the guides on which the film changer is mounted for moving between active and inactive positions.

DESCRIPTION OF A PREFERRED EMBODIMENT

Figure 1:
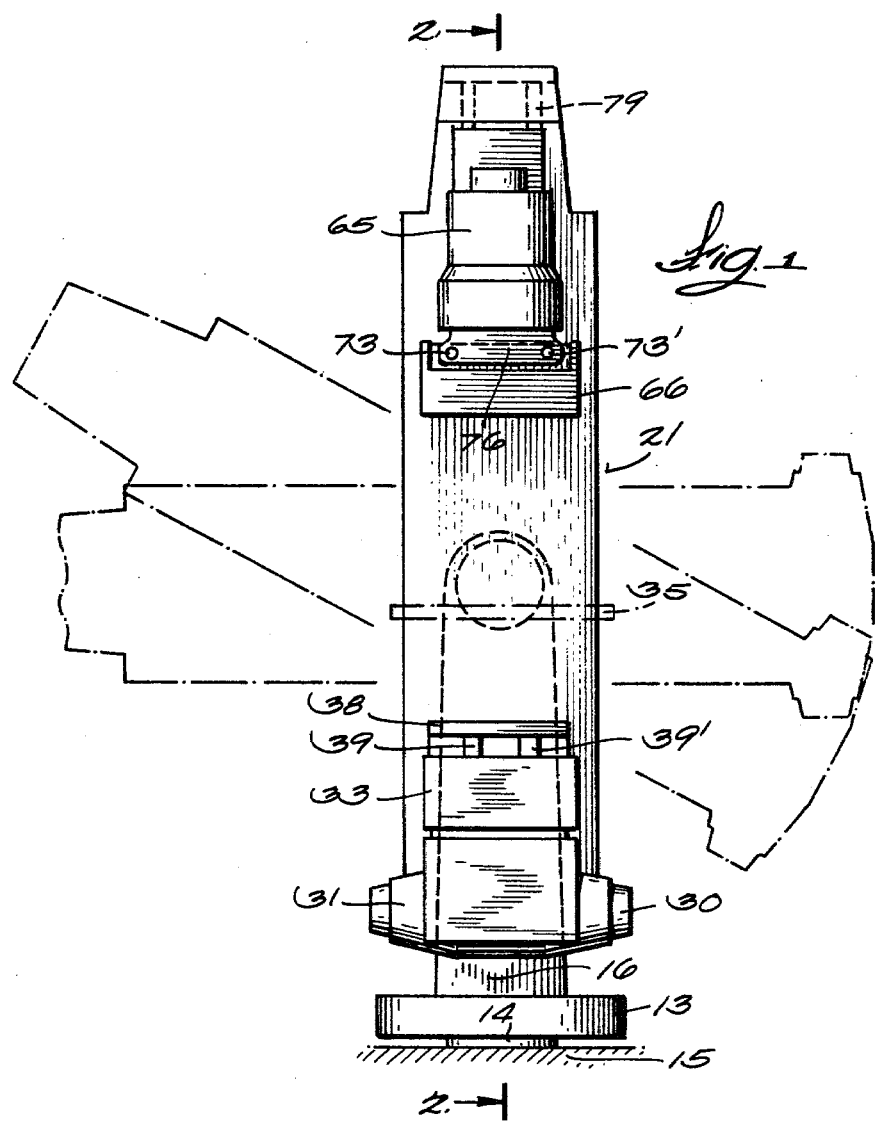
FIG. 1 is a front elevation view of the improved multiaxial x-ray apparatus.

Referring to FIG. 2, a gantry for supporting an x-ray image intensifier, a film changer and an x-ray source for multiaxial angiography comprises an L-shaped member, which is generally designated by the numeral 10.

An x-ray source, generally designated by the numeral 30 is mounted at the end of U-arm leg 25 for projecting an x-ray beam whose cenral ray or axis is coincident with the vertical axis of rotation of the L-arm in its bearing 14. The x-ray source comprises an x-ray tube casing 31 which contains a rotary anode x-ray tube, not visible in FIGS. 1 or 2. The level of the focal spot on the x-ray tube target is at about the level of the point marked 32 on the casing but the focal spot lies on the vertical rotational axis of the gantry. An x-ray beam defining collimator 33 is mounted to the x-ray tube casing and defines the boundaries of the x-ray beam which is projected through a patient 34 who lies supinely on an x-ray transmissive table top 35 which is supported in cantilever fashion by means which are not shown but are familiar to those skilled in the art. The x-ray beam and coincident vertical rotation axis is represented by a line marked 36. The point at which the axis and the horizontal axis 20 for U-arm rotation intersect is the isocentric point which is marked 37. For substantially all angiographic procedures which may be contemplated, the patient 34 is kept fixed coincident with the isocenter 37 which is at about the center of the patient's body when the patient is set up for examination. By combining rotational angles of the L-arm support 10 and U-arm 18, the x-ray beam axis may be directed in the posterior-anterior (PA) aspect at a variety of caudal, cranial and oblique angles as well as true lateral orientations relative to the patient which facilitates obtaining plan views of blood vessels and surrounding anatomy lying in almost any plane.

X-ray source 30 is mounted for moving radially inwardly and outwardly relative to horizontal rotational axis 20 and, hence, isocenter 37. Thus, as can be seen in FIGS. 2 and 3, the x-ray source is mounted to a carriage 38 which has fixed in it a pair of guide rods or shafts 39 and 39'. The guide rods slide in linear bearings such as the one marked 40 which are mounted in a support member 49 that is fastened to the outer end of the U-arm leg member 25. Thus, the rods and carriage 38 can move lengthwise to enable the x-ray source which it supports, and which can be looked upon basically as being the focal spot 32, to move radially inwardly or outwardly relative to the horizontal U-arm axis 20 and isocenter 37.

The x-ray source carriage 38 and, hence, the source 30 which it carries are fully counterbalanced in the apparatus described herein such that the U-arm 18 will tend to remain in any position to which it has been angulated about its horizontal rotational axis 20 regardless of the radial positon of the x-ray source 30 relative to that axis. Counterbalancing of the x-ray source is achieved by the use of a counterbalancing system including a counterweight 42 which is mounted on guides, not shown, in the base section 21 of the U-arm. A leading or load cable 43 which runs on sheaves 44, 45 and 46 has one of its ends fastened to counterweight 42 at point 47 and the other of its ends fastened to x-ray source carriage 38 at a point marked 48. It will be evident in FIG. 2 that when source 30 is moved radially inwardly, counterweight 42 will move radially outwardly in respect to the axis 20 to maintain balance of the U-arm around its rotational axis 20.

A trailing cable 50 is also provided. One of its purposes is to prevent counterweight 42 from falling freely if the U-arm is rotated more than 90° from vertical and another purpose is to make the counterweight move bi-directionally oppositely of source movements. Trailing cable 50 runs on a pair of sheaves 51 and 52, as schematically illustrated, and has one of its ends fixed at a point 53 to counterweight 42 and the other of its ends fixed at a point 54 to the x-ray source carriage 38. Trailing cable 50 includes a section 55 that is composed of chain. This chain runs over a drive sprocket 56 and is captured between a pair of idler sprockets such as the one marked 57. Drive sprocket 56, as can be seen in FIG. 3, is fastened to a shaft 58 which extends from a slip-clutch 59 that is driven from a small or low-power electric motor 60. Motor 60 is fixedly mounted in U-arm leg member 25 by means which are not shown. The motor and slip-clutch combination is one example of a force limited actuator means alluded to earlier.

Slip-clutch 59 is shown symbolically but is a commercially available type that can be operated selectively electrically to couple motor 60 to drive sprocket 56 and to uncouple the same. When the slip-clutch is caused to couple and reversible motor 60 is energized, chain section 55 and the counterweight cable 50 in series with it will be driven translationally to move the x-ray source 30 in one direction and the counterweight 42 in the opposite direction to maintain balance. The clutch will slip at a predetermined force or resistance if the x-ray source encounters any obstruction. In a practical embodiment, for example, 5 pounds of resistance will result in slippage when the x-ray source is being motor driven. It will be evident that a very small motor 60 and generally low-power drive system is used for the x-ray source since its counterbalancing obviates the need for very much driving power.

As will soon be evident, an occasion for driving the x-ray source with the motor 60 and the clutch 59 in its coupled state is when it is desired to move the source correspondingly with image receptors in order to maintain a constant SID and yet obtain various amounts of magnification of the x-ray image resulting from the anatomy which is in the x-ray beam.

The clutch arrangement also permits the x-ray source to be driven radially independently of the receptors if it is desired to obtain a particular degree of magnification or different degrees of magnification at any SID. Also, when the clutch is not engaged, the x-ray source can be manually positioned as desired.

An x-ray image intensifier 65 and a rapid film changer 66 are mounted for moving radially with respect to axis 20 and isocenter 37 at the end of leg member 24 of the U-arm. The image intensifier may be a well known type that converts an x-ray image to an optical image that can be viewed on a television monitor, not shown, when fluoroscopy is being conducted. The x-ray image of the patient's anatomy is formed on an image plane in the intensifier which is represented by the dashed line marked 67. Rapid film changer 66 is also a well known type which, in the commercial embodiment, is a type known by the name of Puck and is available from Elema-Schonander, Inc. The film changer has a removable radiographic film magazine 68 from and to which films are dispensed. The image plane of the film in the changer is represented by a dashed line marked 69. When the image intensifier is to be used, the film changer 66 is retracted axially out of alignment with the x-ray beam axis 36 to a position represented by the phantom lines adjacent film magazine 68.

In the FIG. 2 embodiment, the mounting means for the image intensifier and film changer comprises a member 70 which is fastened to the end of the U-arm leg section 24. This is also shown in FIG. 4 which should be considered in conjunction with FIG. 2. A first carriage 71, which supports the film changer, is mounted for moving vertically on member 70 or, more specifically, radially relative to horizontal U-arm axis 20. As can be seen in FIG. 4 particularly well, carriage 71 has a pair of vertically extending rods 72 and 72' attached to it which constrain the carriage to move linearly in complementarily shaped linear bearings within stationary member 70. The mounting for the film changer 55, as shown in FIG. 2, also includes two pairs of linear bearings 74 and 75 which are mounted to carriage 71. The film changer 66 is mounted to a support member 76 that has a pair of parallel axially directed rods 73 and 73' fastened to it. The rods 73 and 73' pass through linear bearings 74 in such a way that film changer 66 may move axially between its inactive or parked position and its active position where it is aligned with the x-ray beam axis. The motor drive for shifting the film changer between inactive and active positions is not shown in the FIGS. 1-4 embodiment since this can be devised easily by a mechanical designer. The film changer can simply be shifted manually if desired.

The image intensifier 65 in the FIGS. 2 and 4 embodiments, is mounted to a carriage 77 which is slidable or movable linearly on carriage 71. As can be seen particularly well in FIG. 4, the image intensifier carriage 77 is movable on a pair of guide rods 78 and 79 which are fastened to carriage 71. Carriage 77 slides on these rods when the image intensifier has a force applied to it for moving it radially relative to the isocenter and the x-ray source as required for establishing the desired amount of image magnification and radial outward retraction of the carriage 77 and the intensifier allows the film changer to be shifted forward to its active position as depicted in FIG. 2.

Film changer 66 is shown in phantom lines in FIG. 2 where it is positioned for contact or low magnification radiography. It will be evident that the image intensifier will, at this time, follow the vertical or radial movement of the film changer, because one carriage is mounted to the other, and will reach a position where it is represented in phantom lines in FIG. 2 above the phantom of the film changer. Now if the physician should want to switch from film changer radiography to image intensifier fluoroscopy, the film changer can be rapidly retracted axially or rearwardly with it supporting guide rods 73 in linear bearings 74, 75 and the intensifier can be moved further radially inwardly along with its carriage to dispose its image plane 67 substantially at the same distance from the isocenter 37 as the image plane 69 of the film changer was previously located. The distance that the intensifier can travel is additive to the distance that the film changer travels radially which results from the intensifier carriage 77 being mounted to the film changer carriage 71. This extended movement is desirable because then the intensifier does not have to travel so far to be in the same location as the film changer after the latter is used.

The film changer 66 and image intensifier 65 assemblies are also fully counterbalanced and subject to manual radial adjustment and, alternatively, to motor assisted radial adjustment. The counterbalancing and drive systems for the intensifier and film changer will now be described. The counterbalancing system for the film changer 66 and its carriage 71 comprises a counterweight 81 in the base section of the U-arm. A cable 82 runs on a pair of sheaves 83 and 84, the latter of which is mounted for rotation on fixed member 70 as can be seen in FIGS. 2 and 4. One end of cable 82 is fastened at a point marked 85 to counterweight 81 and the other end is fastened to film changer carriage at a point marked 86. The film changer carriage 71 also has a trailing counterweight cable system comprising a cable 87 whose one end is fastened to the upper portion of the film changer carriage at a point marked 88. Cable 87 runs on sheaves 89, which is behind sheave 84, and on sheaves 90, 91 and returns to the bottom end of counterweight 81 where it is attached at a point marked 92. Trailing cable 87 has a chain section 93 in it which engages with a sprocket 94. As can be seen in FIG. 3 particularly well, sprocket 94 is carried on a shaft 95 which extends from a force limiting coupling such as a slip-clutch that is shown symbolically and is marked 96. The clutch is for coupling and uncoupling the shaft of a small electric motor 97 to and from drive chain section 93. It will be evident that energization of motor 97 and its rotation in one direction or another will result in film changer carriage 71 and counterweight 81 being actuated or moved radially under power assist. Moreover, the film changer carriage 71 and film changer thereon can be actuated or moved radially inwardly and outwardly relative to the isocenter solely under manual force in which case the counterweight 81 will still move in the proper direction for maintaining the U-arm in a counterbalanced condition regardless of its angular attitude and regardless of the radial location of the film changer.

The image intensifier 65 and its carriage 77 are also independently counterbalanced by use of a counterweight 100 which is also located in the hollow base section 21 of the U-arm. The guides for counterweight 100 and 81 as well are not shown but should be understood to be present. Image intensifier counterweight 100 uses a load cable 101 which is fastened at its end at a point marked 102 to counterweight 100. Cable 101 runs on a series of sheaves 103, another sheave 103' and a sheave 104 after which it connects to the image intensifier carriage 77 at a point marked 105. A trailing cable 106 is also provided for the image intensifier counterbalancing system. It runs on a sheave 107 and has one end attached to the intensifier carriage 77 at a point marked 108. Trailing cable 106 also runs on additional sheaves 109 and 110 after which it includes a chain section 111 that passes around and is engaged with a sprocket 112. The chain section converts to cable again and is shown broken away but continues to a point 113 where it is fastened to counterweight 100. The sprocket 112, as can be seen in FIG. 3, is coupled to a driving force limiting device such as an electrically operated slip-clutch 114 which is driven from a low-power motor 115. The characteristics of the counterbalancing and drive system for the image intensifier 65 are comparable to those which have been explained in reference to the film changer system so the description need not be repeated in detail.

Force limited actuator systems other than the motor and slip-clutch combinations that have been described in detail can be employed for moving the image intensifier, film changer or x-ray source radially with motor power and for allowing any of these components to be moved manually without substantial opposing force being encountered. By way of example, consider the actuator for the image intensifier 65 which, in the FIGS. 1-4 embodiment and others to be described uses a motor 97 and a slip-clutch 96 to turn a sprocket 94 which engages a chain section 93 in the counterweight trailing cable 87 to drive and to permit reverse movement under manual influence. The clutch can be eliminated, for example, and direct motor drive can be made if the reversible motor 97 chosen is of the commercially available type which delivers a certain limited torque in a selected direction and can be stalled or forced to rotate reversely without drawing thermally damaging current. Actuating the intensifier, changer or source with a motor of this type allows limiting the force if one of these components is driven into an obstruction and it also permits the motor to be overhauled easily when it is deenergized and the component is moved manually. It should be evident that a speed reducer containing a gear train would be an undesirable thing to interpose between the drive sprocket and motor shaft because this would cause too much resistance and, if the reducer contained a worm and wheel, would prohibit overhauling or reverse rotation of the motors in response to manual movements of the intensifier, source or film changer.

Now that the structural features of the FIGS. 1-3 embodiment have been described, the unique functional features will be summarized. One significant feature is that the gantry, particularly the U-arm, always remains in balance regardless of the rotational angle of the U-arm. This results from the fact that the x-ray image intensifier, the rapid film changer and the x-ray source are all independently counterbalanced so the movement of any one of them cannot upset the balance.

The provision for manual and, optionally, motor assisted radial positioning of the image intensifier, the film changer and the x-ray source enables all of the image producing devices to be located properly for making an x-ray exposure even if a motor fails. This can avoid interruption of an x-ray examination and any necessity for awaiting servicing of the equipment before the examination can be resumed. As has been pointed out, in prior art angiographic apparatus, lacking the counterbalancing features of the apparatus described herein, the film changer, intensifier, and possibly the x-ray source, must be driven with enough motor power to overcome the full weight of any of these elements which means that, in order to avoid using a huge motor, a gear reduction system must be interposed between the motor and the element that is driven. Thus, if a motor fails in the prior equipment, the element which it drives cannot be moved manually since it is impossible to apply enough force to make the gear reduction system or other positive mechanical drive operate in reverse. In the apparatus described herein each of the described motions, being fully counterbalanced, can be operated manually easily. A concomitant of this is that, in the described apparatus, when any component is being motor driven and the corresponding clutch is engaged the clutch will slip if the intensifier, film changer or x-ray source is driven into contact with the patient or other obstruction. Risk of injury to the patient and the likelihood of damage to the equipment is thereby significantly reduced where force limited actuation is used as in the invention as compared with prior art angiographic apparatus.

One of the most important features of the apparatus is that it permits obtaining x-ray images through the agency of the film changer or image intensifier at a plurality of magnifications and at a constant SID, if desired. It is only necessary to establish the desired SID with one or the other of the intensifier or film changer image receptors at a specific distance from the x-ray source. Then, if x-ray views are desired at different magnifications, the source and receptor can be driven synchronously in radially opposite directions by simply running the x-ray source drive motor and one of the receptor drive motors at the same time. Moreover, contact imaging, that is, having a receptor in contact with or near the patient for obtaining a low amount of magnification is also easily obtainable. This results from the fact that the intensifier and film changer are independently movable as is the x-ray source. Moreover, it is easy to place the image plane of one receptor exactly at the place where the image plane of the other receptor was located in connection with switching between the radiographic and fluoroscopic modes.

A modified structure for supporting the image intensifier and film changer will now be described in reference to FIGS. 5-7. Parts which are similar to those in the FIGS. 1-3 embodiment are given the same reference numerals. Thus, the U-arm comprises a base section 21 and an axially extending leg section 24 as shown in FIG. 5. The image intensifier 65 is supported on a carriage in the other embodiment. Carriage 120 is provided with a pair of parallel guide rods one of which, 121 is visible in FIG. 5 and the other of which is behind it. Rod 121 and its counterpart are slidable in bearings 122 installed at the end of leg section 24. Carriage 120 is counterbalanced with the use of a counterweight similar to any of those shown in the previous embodiment. In FIG. 5, a fragment of the load counterweight cable 123 is visible. It runs on a sheave 124 and is attached to carriage 120 at a point marked 125. The trailing cable 126 runs on a sheave behind sheave 124 and is attached to carriage 120 at a point marked 127.

The film changer 66 support comprises a platform 130 to which there are four guide rods attached, two of which, 131 and 132 are visible in FIG. 5 and there are corresponding rods behind them which are not visible. The guide rods 131 and 132 run through bushings such as the one marked 134. A parallel pair of axially extending guide rods such as the one marked 135 in FIG. 5 are mounted to the bottom of the platform on studs such as the one marked 136 in FIG. 7. A planar member 137 shown in FIG. 5 is provided with bearing elements 138 which enables the film changer to move axially on rods 135 from the active position of the film changer in which it is shown in FIG. 5 to inactive or parked position closer to U-arm base section 21.

Film changer 66 is motor-driven along guide rods 135 between parked and active positions. For this purpose, the member 137 has a gear rack 139 fastened on its top. The gear rack, as can be seen clearly in FIG. 6, is driven by a pinion 140 which is fastened to the lower end of a shaft 142 which appears in FIG. 5. The lower end of shaft 142 is cylindrical for passing through a bushing 141 that is fixed in platform 130. The part of shaft 142 above bushing 141 is square in cross section and, extends slidably through the square central holes in another pinion 143. Pinion 143 is driven from a gear 144 on a motor 145. The motor is effectively mounted to leg section 24. Making the shaft 142 and the hole in pinion 143 square enables the shaft to be driven and to move when the platform is moved on guide rods 131 and 132.

In the FIGS. 5-7 embodiment, the x-ray source would be mounted on the U-arm along with its counterbalancing means in the same fashion in which it is mounted in the FIGS. 1-4 embodiment.

In summary, each of the embodiments provide for motor assisted and manual radial adjustment of the image receptors and the x-ray source. In each embodiment, the receptors and source are independently counterbalanced. In all cases, substantially unmagnified and magnified images are obtainable without shifting the patient away from the isocenter. Moreover, any amount of magnification within the limits of the apparatus can be obtained while a constant source-to-image distance is maintained. The gantry, comprised of a member rotatable about a vertical axis and a U-arm rotatable on it about a horizontal axis, is maintained in rotational balance for all positions of the receptors and source and for all angulations of the x-ray beam axis with respect to a patient who is supported in coincidence with the isocenter.

We claim:

1. X-ray apparatus for making angiographic examinations of a human body, comprising,
a support rotatable about a vertical axis, a U-arm including a base section mounted to the support for rotation about a horizontal axis, said U-arm having leg sections extending from each of the opposite ends of said base section in substantial parallelism with each other and with the rotational axis of the base section, the horizontal axis about which the U-arm rotates and the vertical axis about which the support rotates intersecting each other at a point designated as an isocenter at which said body would be located for angiography, X-ray source means and means supporting said source means for moving substantially perpendicular to one of the axial extending leg sections and radially relative to said horizontal axis, said source means being arranged to project an x-ray beam along an axis that is coincident with the vertical axis and intersects said isocenter, counterweight means and means coupling said counterweight means to said means for supporting said source means for moving jointly relative to said horizontal axis to counterbalance said source means and its supporting means in all of its radial positions, a film changer and means supporting said changer for moving substantially perpendicular to the other of said U-arm leg sections and radially relative to said horizontal axis, and means for mounting said changer to said supporting means for moving axially between positions in which said changer is selectively in or out of alignment with said x-ray beam axis, counterweight means and means coupling said counterweight means to said means for supporting said film changer for moving jointly relative to said horizontal axis to counterbalance said film changer and its supporting means in all of its radial positions, an image intensifier and means supporting said intensifier for moving substantially perpendicular to said other of the U-arm leg sections and radially relative to said horizontal axis, and counterweight means and means coupling said counterweight means to said means for supporting said intensifier for moving jointly relative to said horizontal axis to counterbalance said intensifier and its supporting means in all of its radial positions.

2. The apparatus as in claim 1 wherein:

said means for supporting said film changer comprises a first carriage supported for moving radially on said other U-arm leg section and the means for mounting the film changer for moving axially is mounted to said carriage, and said means for supporting the image intensifier comprises a second carriage supported for moving radially on said other U-arm leg section adjacent and in parallelism with the first carriage and the intensifier is mounted to the second carriage.

3. The apparatus as in claim 1 wherein:

said means for supporting the film changer comprises a first carriage supported for moving radially on said other U-arm leg section and said means for mounting the changer for moving axially is mounted to the carriage, and said means for supporting said intensifier comprises a second carriage mounted to the first carriage for moving radially and said intensifier is mounted to the second carriage such that the intensifier will move radially through the distance in which said first carriage moves relative to said other leg section plus the distance through which the second carriage moves relative to the first carriage.

4. The apparatus defined in any of claims 1, 2 or 3 including:

three force limited actuator means for delivering a limited force when activated and for yielding to a predetermined force, said actuator means being coupled, respectively, to said movable image intensifier, film changer and x-ray source supporting means for moving the source, intensifier or changer and their respective counterweight means when said actuator means is activated and for responding to said predetermined force resulting from obstructing or manually moving any of said source, intensifier or film changer by yielding.

5. The apparatus defined in any of claims 1, 2 or 3 including:

a plurality of actuator means for providing a limited driving force in a selected direction and for yielding to a predetermined force in said selected direction and to a predetermined force in an opposed direction, means for coupling said actuator means in driving relation to said x-ray source, film changer and intensifier supporting means, respectively, to enable said actuator means to move the source, changer and intensifier supporting means to which the actuator means is coupled to and move simultaneously the counterweight means that are coupled to the respective supporting means and to enable said actuator means to yield in response to movement of said source, changer or intensifier being obstructed and to yield in response to the source, changer or intenifier being moved under influence of a manual force in either radial direction.

6. The apparatus defined in claim 4 wherein said force limited actuator means comprises three motors and a clutch for each motor, each clutch being operable to couple and uncouple its motor to and from the corresponding image intensifier, film changer and x-ray source counterweight means such that when a motor is operated while its clutch is coupled, the intensifier, film changer or x-ray source and corresponding counterweight means will move and such that when a motor is uncoupled or coupled manual movement of the intensifier, film changer or x-ray source will move the corresponding counterweight means to maintain the balance of the U-arm about its rotational axis.

7. The apparatus as in claim 4 wherein said force limited actuator means comprises three motors and a slip-clutch for each motor, each clutch being operable to couple and uncouple its motor to and from the corresponding image intensifier, film changer and x-ray source counterweight means, each clutch being adjusted to slip when movement of the respective intensifier, changer or source to which it is effectively coupled is interfered with while the motor is energized and to slip when coupled while said motor is energized or deenergized and the respective intensifier, changer or source is moved manually.

8. The apparatus as in claim 1 including:

a plurality of actuator means and means for coupling the actuator means in driving relationship, respectively, with said means for supporting the x-ray source and with said means for supporting the film changer for said actuator means to drive a selected one of said x-ray source and film changer radially inwardly and the other correspondingly radially outwardly to thereby provide for obtaining various amounts of magnification at a constant source-to-image distance while the body under examination remains coincident with the isocenter.

9. The apparatus as in claim 1 including:
actuator means and means for coupling said actuator means in driving relationship, respectively, with said means for supporting the x-ray source and with said means for supporting the image intensifier for said actuator means to drive a selected one of the x-ray source and intensifier radially inwardly and the other radially correspondingly radially outwardly to thereby provide for obtaining various amounts of magnification at a constant source-to-image distance while the body under examination remains coincident with the isocenter.

10. The apparatus as in claim 1 including:
one reversible motor and means including clutch means operable to couple said motor in driving relationship with said means for supporting the x-ray source and to uncouple said motor, operation of said motor in one direction when said clutch means is coupled causing said x-ray source to move radially inwardly and in the opposite direction causing said source to move radially outwardly,
another reversible motor and means including another clutch means operable to couple said other motor in driving relationship with said means for supporting the film changer and to uncouple said motor, operation of said other motor in one direction when said other clutch means is coupled causing the film changer to move radially inwardly and in the opposite direction causing said changer to move radially outwardly,
operation of one motor in one direction and the other in the other direction at the same time while each of the clutch means are coupled causing one of said changer and intensifier to move radially inwardly and the other to move correspondingly radially outwardly enabling obtaining various amounts of magnification at a constant source-to-image distance while the body under examination remains coincident with said isocenter.

11. The apparatus as in claim 1 including:
one reversible motor and means including clutch means operable to couple said motor in driving relationship with said means for supporting the x-ray source and to uncouple said motor, operation of said motor in one direction when said clutch means is coupled causing said x-ray source to move radially inwardly and in the opposite direction causing said source to move radially outwardly,
another reversible motor and means including another clutch means operable to couple said other motor in driving relationship with said means for supporting the image intensifier and to uncouple said motor, operation of said other motor in one direction when said other clutch means is coupled causing the image intensifier to move radially inwardly and in the opposite direction causing said changer to move radially outwardly,
operation of one motor in one direction and the other in the other direction at the same time while each of the clutch means are coupled causing one of said x-ray source and intensifier to move radially inwardly and the other to move correspondingly radially outwardly enabling obtaining various amounts of magnification at a constant source-to-image distance while the body under examination remains coincident with said isocenter.

12. Apparatus for enabling making angiographic images of anatomy at a multiplicity of angular aspects with selected amounts of magnification using an x-ray source coacting alternatively with a radiographic film changer and an x-ray image intensifier without requiring that the anatomy of interest be moved relative to an isocenter at which the anatomy is located, comprising:
an L-arm including a vertical section and a horizontal section extending from one of the ends of the vertical section, the horizontal section being supported for rotating about a vertical axis,
a U-arm including a base section mounted on the end of the vertical L-arm section for rotation about a horizontal axis that intersects the vertical axis of the L-arm at a point defined as the isocenter, and a leg section extending from each of the opposite ends of the base section generally parallel to each other and to the rotational axis of the base section,
an x-ray source carriage mounted at the end of one of the U-arm leg sections for moving radially inwardly and outwardly and generally perpendicular relative to the rotational axis of the U-arm and an x-ray source mounted to the carriage and operable to project an x-ray beam along an axis extending through said isocenter,
an x-ray image intensifier carriage and a film changer carriage and means for mounting said carriages for moving at the end of the other of said U-arm legs radially inwardly and outwardly and perpendicularly relative to said horizontal axis,
an x-ray image intensifier mounted to said intensifier carriage for said intensifier to be movable toward and away from said isocenter and in alignment with said source,
support means mounted to said film changer carriage and a film changer mounted on said support means for moving parallel to said horizontal axis between an inactive position out of alignment with the x-ray beam axis and an active position where it is aligned with the x-ray beam axis and said changer being movable radially with said carriage toward and away from said isocenter and source,
a plurality of counterweight means each of which is located in said U-arm and is movable independently of the others relative to the horizontal axis of said U-arm, and
means operatively coupling said counterweight means respectively to said image intensifier carriage, said film changer carriage and said x-ray source carriage to effect movements of said counterweights in coordination with movements of said intensifier, film changer or source, respectively, to thereby maintain the balance of said U-arm for any angulation of the U-arm.

13. The apparatus defined in claim 12 including:
a motor and means including a clutch for selectively coupling and uncoupling said motor in and out of driving relation with the counterweight means for said image intensifier, coupling by said clutch enabling said motor to cause coordinate movement of said image intensifier and its counterweight means, and uncoupling by said clutch enabling said counterweight means to move coordinately with the image intensifier in response to manual movement of the image intensifier.

14. The apparatus defined in claim 13 including:
a motor and means including a clutch for selectively coupling and uncoupling said motor in and out of driving relation with the counterweight means for said film changer, coupling by said clutch enabling said motor to cause coordinate movement of said film changer and its counterweight means, and uncoupling by said clutch enabling said counterweight means to move coordinately with said film changer in response to manual movement of the film changer.

15. The apparatus defined in claim 13 including:
a motor and means including a clutch for selectively coupling and uncoupling said motor in and out of driving relation with the counterweight means for said x-ray source, coupling by said clutch enabling said motor to cause coordinate movement of said x-ray source and its counterweight means, and uncoupling said clutch enabling said counterweight means to move coordinately with said x-ray source in response to manual movement of the x-ray source.

* * * * *